(12) United States Patent
Gianchandani et al.

(10) Patent No.: US 12,044,609 B2
(45) Date of Patent: Jul. 23, 2024

(54) DISTRIBUTED PRESSURE MEASUREMENT SYSTEM FOR CORE FLOOD EXPERIMENTS

(71) Applicants: TOTAL S.E., Courbevoie (FR); THE REGENTS OF THE UNIVERSITY OF MICHIGAN, Ann Arbor, MI (US)

(72) Inventors: Yogesh B. Gianchandani, Ann Arbor, MI (US); Tao Li, Ann Arbor, MI (US); Partha Dutta, Ann Arbor, MI (US); Alexander Benken, Ann Arbor, MI (US); John-Richard Ordonez-Varela, Houston, TX (US)

(73) Assignees: The Regents of The University of Michigan, Ann Arbor, MI (US); TOTAL S.E., Courbevoie (FR)

( * ) Notice: Subject to any disclaimer, the term of this patent is extended or adjusted under 35 U.S.C. 154(b) by 169 days.

(21) Appl. No.: 17/763,733

(22) PCT Filed: Oct. 2, 2020

(86) PCT No.: PCT/US2020/053970
§ 371 (c)(1),
(2) Date: Mar. 25, 2022

(87) PCT Pub. No.: WO2021/067720
PCT Pub. Date: Apr. 8, 2021

(65) Prior Publication Data
US 2022/0326136 A1   Oct. 13, 2022

Related U.S. Application Data

(60) Provisional application No. 62/910,828, filed on Oct. 4, 2019.

(51) Int. Cl.
*G01N 15/08*   (2006.01)
*G01L 15/00*   (2006.01)
(Continued)

(52) U.S. Cl.
CPC .......... *G01N 15/0826* (2013.01); *G01L 15/00* (2013.01); *G01L 19/0038* (2013.01);
(Continued)

(58) Field of Classification Search
CPC ........... G01N 15/0826; G01N 15/0806; G01N 33/24; G01N 2203/0232; G01N 2203/0617; G01L 15/00; G01L 19/0038
See application file for complete search history.

(56) References Cited

U.S. PATENT DOCUMENTS 5,095,273 A * 3/1992 Kennedy .............. G01N 27/043
73/152.11
5,164,672 A * 11/1992 Gilliland .............. G01N 33/241
73/152.09

(Continued)

FOREIGN PATENT DOCUMENTS

CN         108287123 A      7/2018
EP         4137793 A1 *     2/2023  ............... G01F 1/34

OTHER PUBLICATIONS

EP-4137793-A1, English Translation (Year: 2023).*
(Continued)

*Primary Examiner* — Ryan D Walsh
(74) *Attorney, Agent, or Firm* — Harness, Dickey & Pierce, P.L.C.

(57) ABSTRACT

Investigating the permeability and porosity of geological samples is a routine element of geological studies, and is of particular interest in the oil and gas industry. Core-flood experiments are commonly performed on rock samples to measure transport characteristics in the laboratory. This disclosure reports the design and implementation of a high resolution distributed pressure measurement system for core-flood experiments. A series of microfabricated pressure sensors can be embedded in bolts that are housed within the pressurized polymer sheath that encases a rock core. A
(Continued)

feedthrough technology has been developed to provide lead transfer between the sensors and system electronics across a 230-bar pressure difference. The system has been successfully benchtop tested with fluids such as synthetic oil and/or gas. Pressure measurements were recorded over a dynamic range of 20 bar with a resolution as small as 0.3 mbar.

20 Claims, 15 Drawing Sheets

(51) Int. Cl.
  *G01L 19/00* (2006.01)
  *G01N 33/24* (2006.01)
(52) U.S. Cl.
  CPC ......... *G01N 15/0806* (2013.01); *G01N 33/24* (2013.01); *G01N 2203/0232* (2013.01); *G01N 2203/0617* (2013.01)

(56) References Cited

U.S. PATENT DOCUMENTS

| | | | |
|---|---|---|---|
| 5,493,226 | A | 2/1996 | Honarpour et al. |
| 5,679,885 | A * | 10/1997 | Lenormand ............ G01N 29/07 73/152.06 |
| 5,698,772 | A | 12/1997 | Deruyter et al. |
| 11,327,000 | B2 * | 5/2022 | Karimi ................. G01N 15/082 |
| 2010/0126266 | A1 | 5/2010 | Coenen |
| 2012/0078541 | A1 | 3/2012 | Hesketh et al. |
| 2016/0109334 | A1 | 4/2016 | Collins et al. |
| 2018/0120476 | A1 | 5/2018 | Yang et al. |

OTHER PUBLICATIONS

International Search Report and Written Opinion of the International Searching Authority issued in PCT/US2020/053970, mailed Dec. 7, 2020; ISA/US.

* cited by examiner

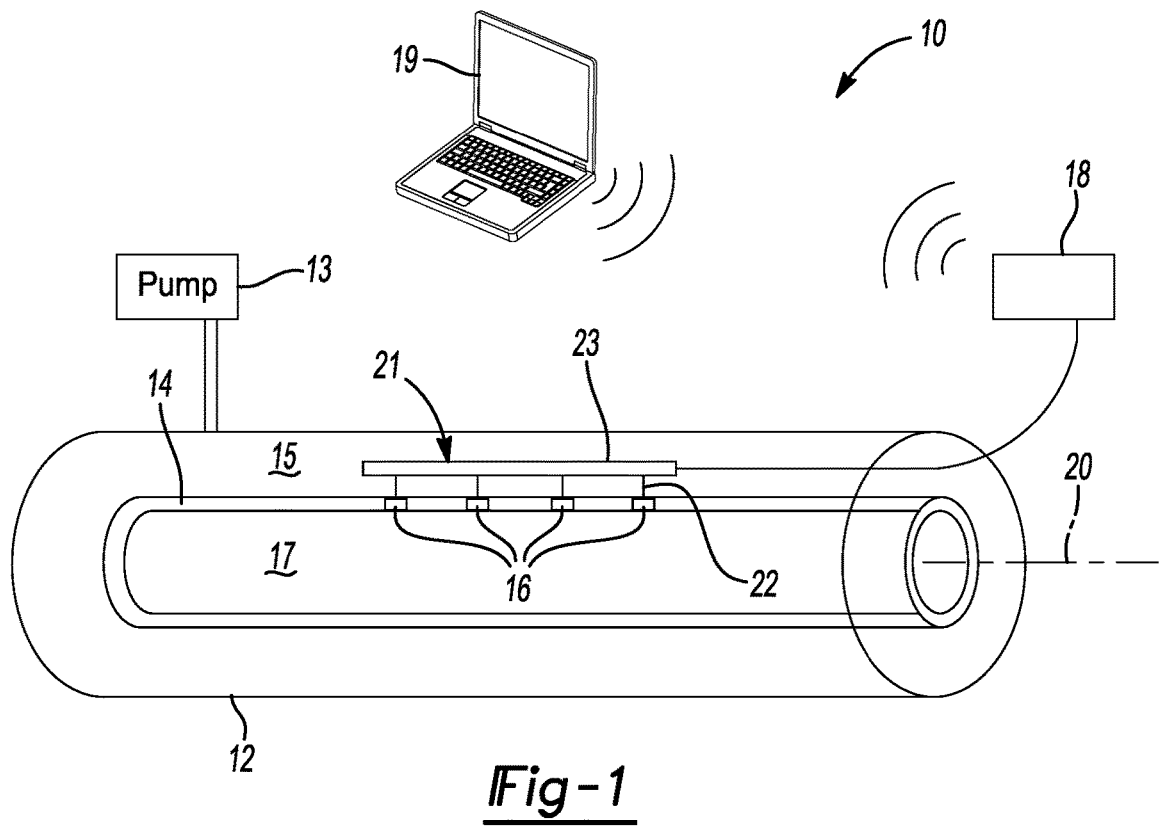
Fig-1
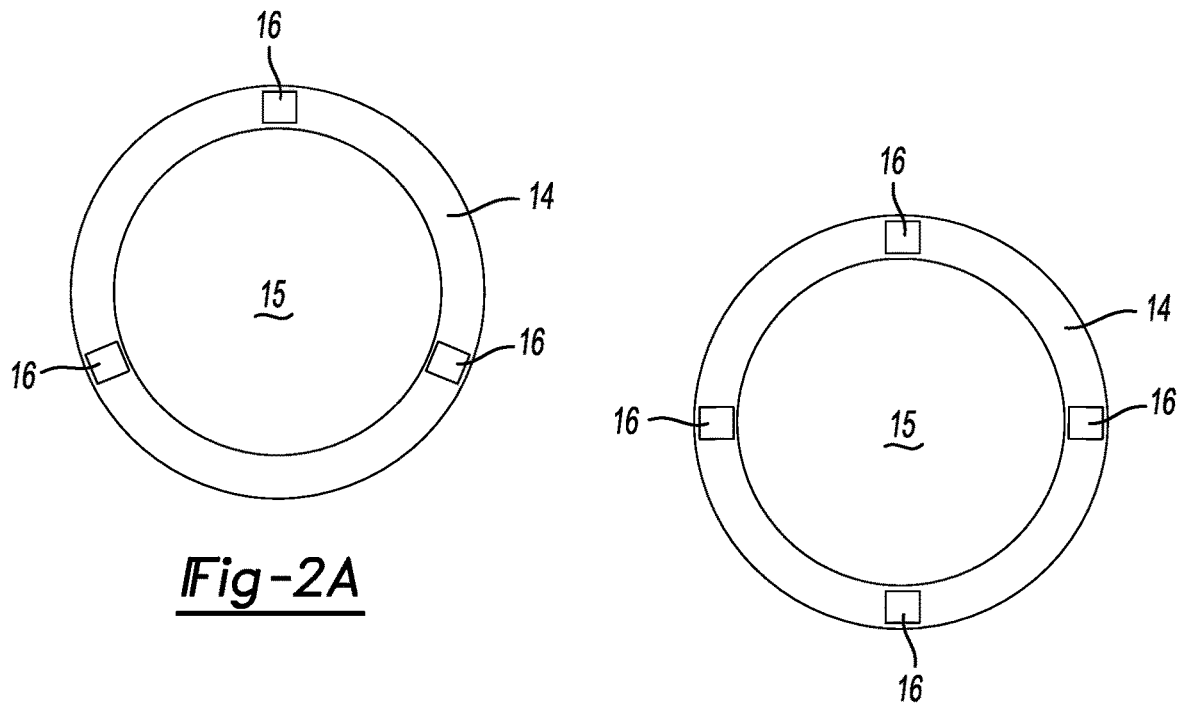
Fig-2A                    Fig-2B

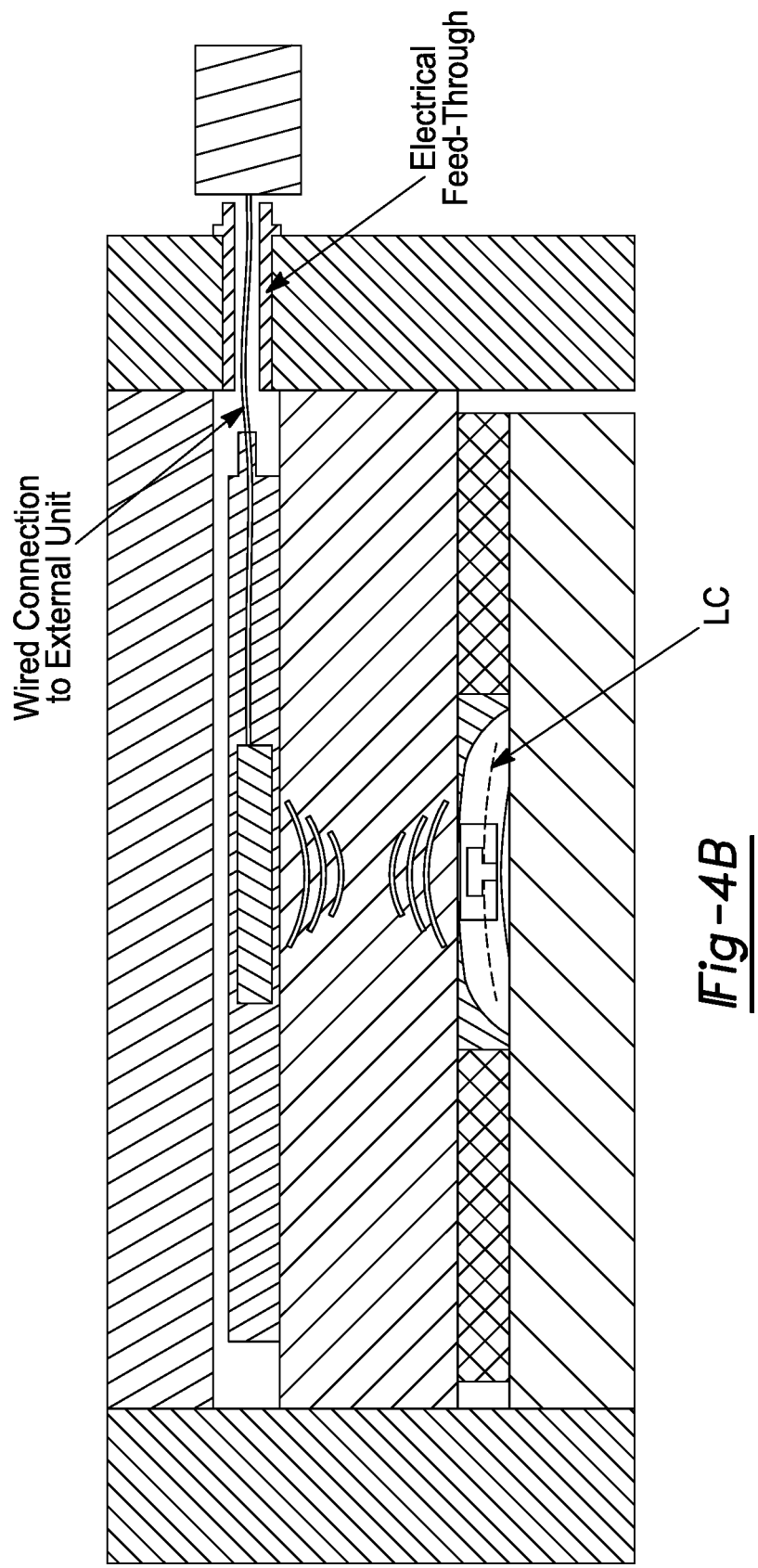

DISTRIBUTED PRESSURE MEASUREMENT SYSTEM FOR CORE FLOOD EXPERIMENTS

CROSS-REFERENCE TO RELATED APPLICATION

This application is a 371 U.S. National Phase of International Application PCT/US2020/053970, filed on Oct. 2, 2020, which claims the benefit of U.S. Provisional Application No. 62/910,828, filed on Oct. 4, 2019. The entire disclosures of the above applications are incorporated herein by reference.

FIELD

The present disclosure relates to a distributed pressure measurement system for performing core-flood experiments.

BACKGROUND

The transport of fluids through porous rocks and the study of such fluid movement is relevant in several fields, including geology, hydrogeology, and petroleum engineering. For example, forcing fluid into a rock core introduces pressure gradients along the flow path that can provide information on the permeability of the rock core. Conventional methods for such core-flood studies have used X-ray CT scans and/or pressure transducers comprising traditional electret microphones to obtain fluid saturation and rock porosity information and investigate boundary pressures. These techniques, however, are limited in their measuring capabilities. For example, conventional methods are unable to measure a pressure gradient along the length of the rock core. Accordingly, it would be desirable to develop measurement systems and methods that enable the collection of wider varieties of data and which also generally ease data collection.

This section provides background information related to the present disclosure which is not necessarily prior art.

SUMMARY

This section provides a general summary of the disclosure, and is not a comprehensive disclosure of its full scope or all of its features.

In various aspects, the present disclosure provides a distributed pressure measurement system. The distributed pressure measurement system includes an enclosure that defines a high-pressure chamber and a sheath disposed within the high-pressure chamber, where the sheath defines a tube that extends along a longitudinal axis and is configured to receive a core sample. The distributed pressure measurement system further includes a plurality of pressure sensors that are embedded in the sheath and disposed along the longitudinal axis of the tube. Each pressure sensor may be configured to measure pressure at a predetermined position along the surface of the core sample.

In one aspect, the plurality of pressure sensors may measure pressure by detecting changes in electrical capacitance.

In one aspect, the plurality of pressure sensors may be grouped into subsets of pressure sensors such that the pressure sensors in a given subset of pressure sensors are arranged around the longitudinal axis of the tube and symmetrically to each other.

In one aspect, each pressure sensor in a given subset of pressure sensors may be spaced 120 degrees apart from other pressure sensors in the respective subset.

In one aspect, each pressure sensor in a given subset of pressure sensors may be spaced 90 degrees apart from other pressure sensors in the respective subset.

In one aspect, the distributed pressure measurement system may further include at least one receiver circuit, which may be positioned outside of the enclosure. The plurality of pressure sensors may communicate pressure measurements to the at least one receiver circuit.

In one aspect, the distributed pressure measurement system may further includes one or more sensor modules distributed on an interior-facing surface of the sheath. Each sensor module may include at least one pressure sensor of the plurality of pressure sensors disposed on a circuit board and a sense coil formed on the circuit board.

In one aspect, the one or more pressure sensors and the sense coil may form an LC sensor module such that changes in capacitance by the plurality of the pressure sensors can causes a change in resonant frequency of the LC sensor module.

In one aspect, the distributed pressure measurement system may further include one or more readout nodes. The one or more readout nodes may be arranged outside of the sheath, such that each readout node is aligned adjacent to a corresponding sensor module. Each readout node may include a readout coil inductively coupled to the sense coil of the corresponding sensor module and a readout circuit configured to detect changes in resonant frequency of the LC sensor module.

In one aspect, the one or more readout nodes may be disposed on an exterior surface of the sheath and may be configured to communicate with a controller disposed outside of the enclosure.

In one aspect, the plurality of pressure sensors may be encapsulated in a flexible mold.

In one aspect, the distributed pressure measurement system may further include a controller in wired communication with the plurality of pressure sensors. The controller may be disposed outside of the enclosure.

In one aspect, the distributed pressure measurement system may further include a plurality of plugs. Each plug may be received by a feedthrough hole formed in the sheath and may be configured to host one of the plurality of pressure sensors.

In one aspect, the distributed pressure measurement system may further include a circuit board. The circuit board may be disposed on an exterior surface of the sheath and electrically coupled to each of the plurality of pressure sensors.

In various other aspect, the present disclosure provides another example distributed pressure measurement system. The distributed pressure measurement system may include an enclosure that defines a high-pressure chamber and a polymeric sheath disposed within the high-pressure chamber. The polymeric sheath may define a low-pressure chamber that extends along a longitudinal axis and that may be configured to receive a core sample. The distributed pressure measurement system may further include a plurality of pressure sensors. The pressure sensors may be embedded in the sheath and disposed along the longitudinal axis of the low-pressure chamber. The plurality of pressure sensors may be grouped into one or more subsets of pressure sensors. Each subset may include at least one pressure sensor of the plurality of pressure sensors. In each given subset of pressure sensors having two or more pressure sensors the pressure sensors may be arranged around the longitudinal axis of the tube and symmetrically to each other.

In one aspect, the plurality of pressure sensors may measure pressure by detecting changes in electrical capacitance.

In one aspect, the distributed pressure measurement system may further include at least one receiver circuit. The at least one receiver circuit may be positioned outside of the enclosure. The plurality of pressure sensors may communicate pressure measurements to the at least one receiver circuit.

In one aspect, the distributed pressure measurement system may further include one or more sensor modules. The one or more sensor modules may be distributed on an interior-facing surface of the sheath. Each sensor module may include the plurality of pressure sensors disposed on a circuit board and a sense coil formed on the circuit board. The plurality of pressure sensors and the sense coil may form an LC sensor module such that changes in capacitance by the one or more pressure sensors causes a change in resonant frequency of the LC sensor module.

In one aspect, the distributed pressure measurement system may further include one or more readout nodes arranged outside of the sheath, such that each readout node may be aligned adjacent to a corresponding sensor module. Each readout node may include a readout coil inductively coupled to the sense coil of the corresponding sensor module and a readout circuit that may be configured to detect changes in resonant frequency of the LC sensor module.

In one aspect, the one or more readout nodes may be disposed on an exterior surface of the sheath and may be configured to communicate with a controller disposed outside of the enclosure.

Further areas of applicability will become apparent from the description provided herein. The description and specific examples in this summary are intended for purposes of illustration only and are not intended to limit the scope of the present disclosure

DRAWINGS

The drawings described herein are for illustrative purposes only of selected embodiments and not all possible implementations, and are not intended to limit the scope of the present disclosure.

FIG. 1 is an illustration of an example high-resolution distributed pressure measurement system for use in core-flood experiments in accordance with various aspects of the present disclosure;

FIG. 2A is a cross-sectional view of the sheath of the high-resolution distributed pressure measurement system illustrated in FIG. 1, where the pressure sensors embedded in the sheath have a first arrangement;

FIG. 2B is a cross-sectional view of the sheath of the high-resolution distributed pressure measurement system illustrated in FIG. 1, where the pressure sensors embedded in the sheath have a second arrangement;

FIG. 4B is a cross-sectional view of an example LC sensor module and readout printed circuit board ("PCB") as assembled with a rock core;

Figure 10A:
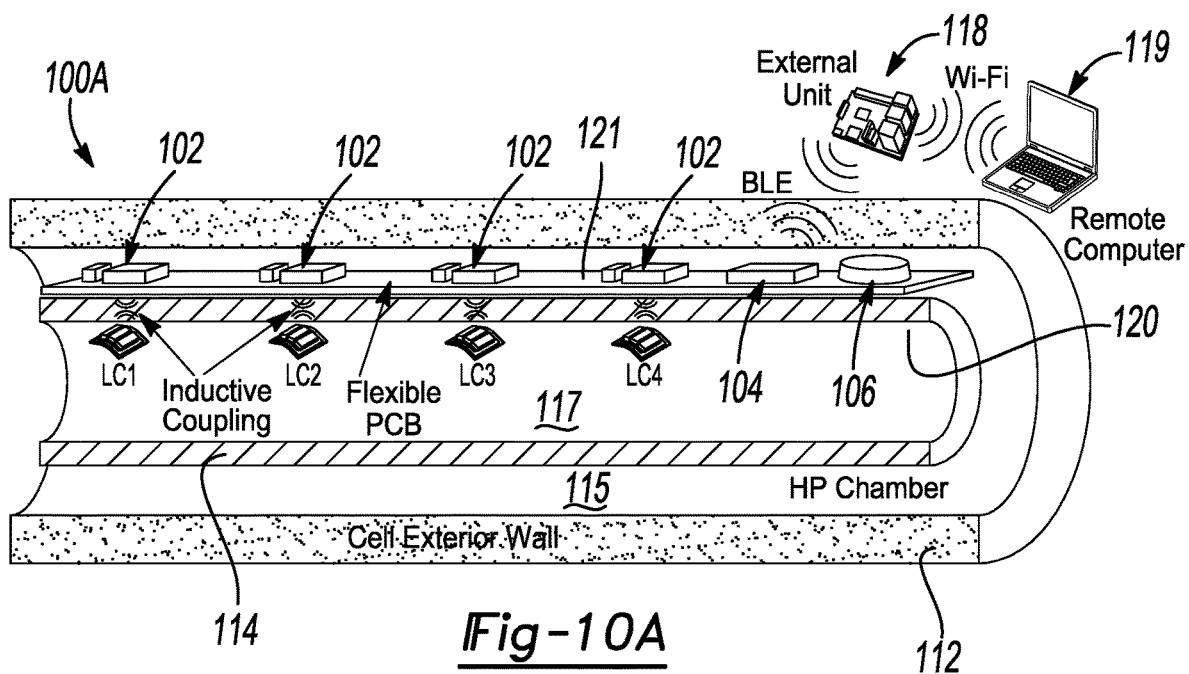
Figure 10B:
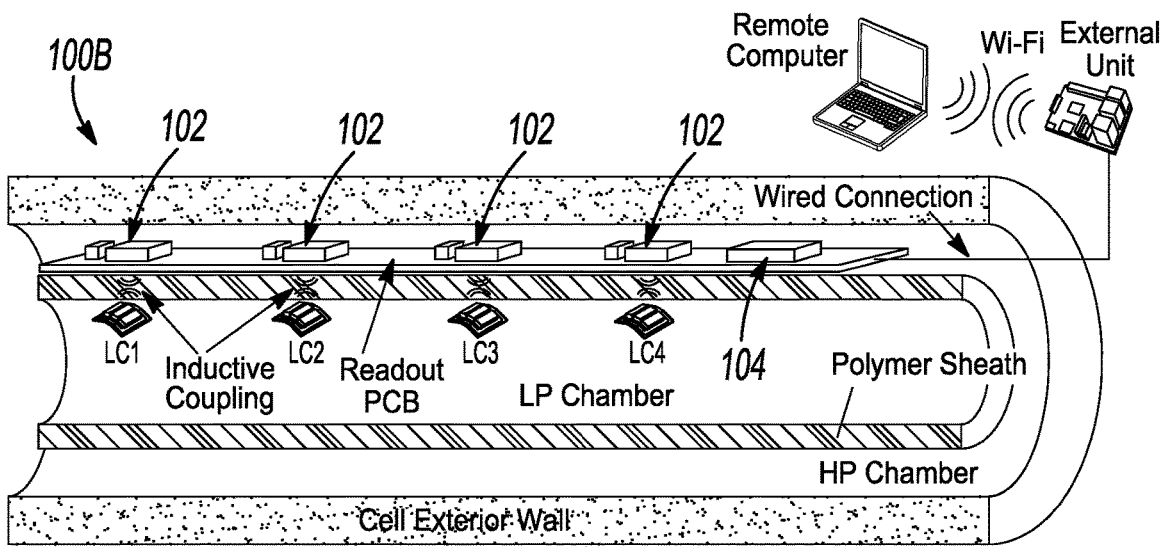

FIG. 10A is a cross-sectional illustration of another example high-resolution distributed pressure measurement system for use in core-flood experiments in accordance with various aspects of the present disclosure; FIG. 10B is a cross-section illustration of another example high-resolution distributed pressure measurement system for use in core-flood experiments in accordance with various aspects of the present disclosure.

Figure 11A:
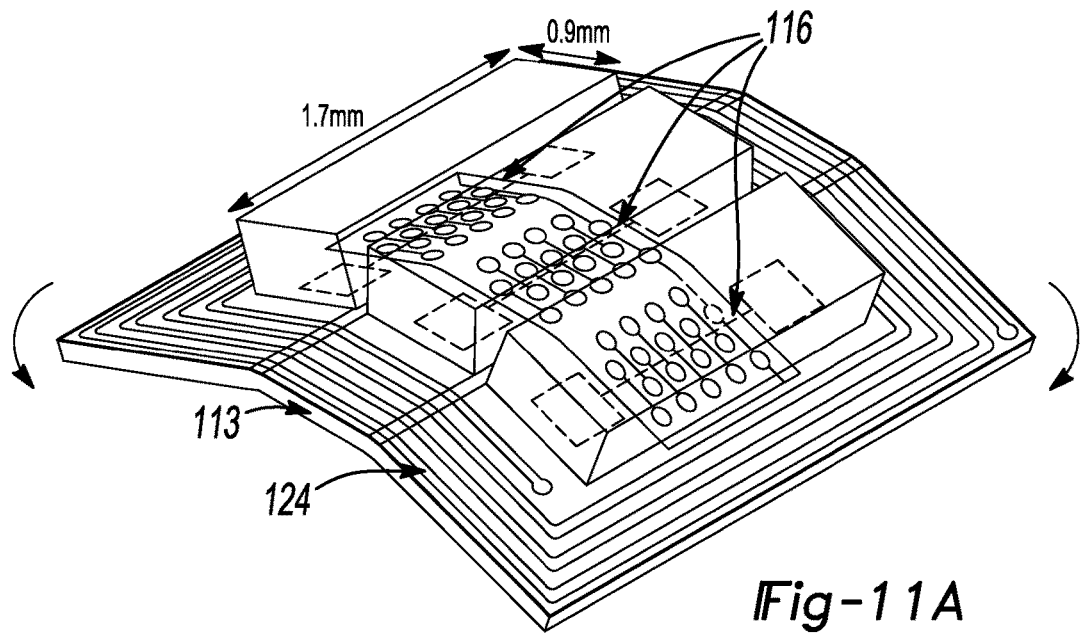
Figure 11B:
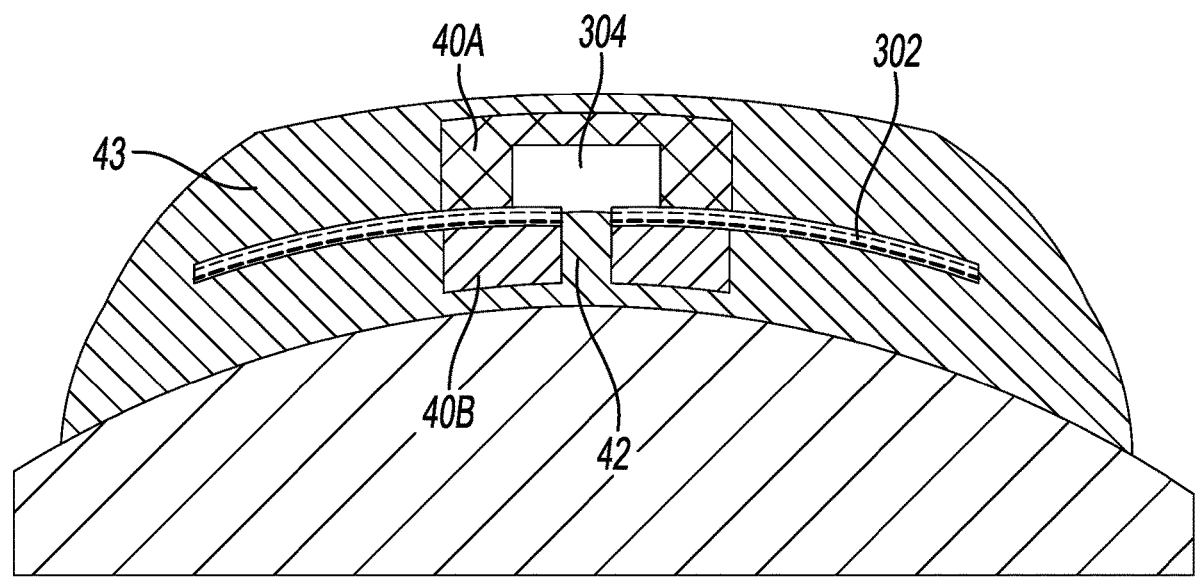
Figure 12:
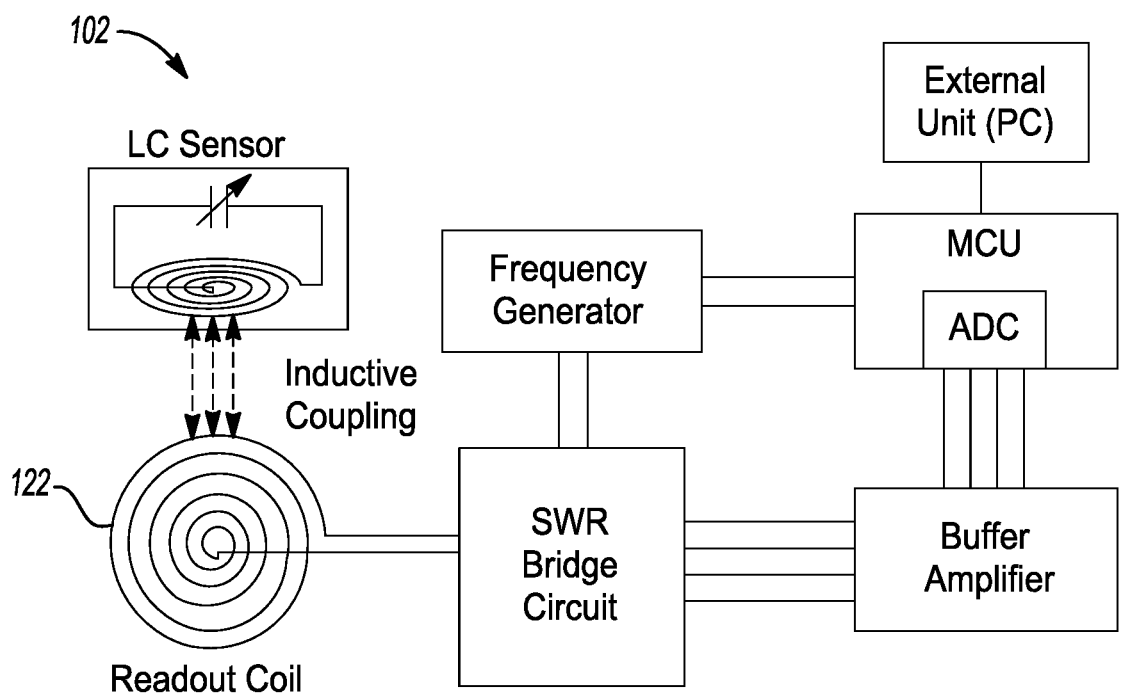

FIG. 11A is a perspective view of an example sensor module as used, for example, in the high-resolution distributed pressure measurement systems, such as illustrated in FIGS. 10A and 10B;

FIG. 11B is a cross-sectional illustration of an example encapsulated sensor module as used, for example, in the high-resolution distributed pressure measurement systems, such as illustrated in FIGS. 10A and 10B; and FIG. 12 is a schematic of an example readout circuit for use with the example high-resolution distributed pressure measurement systems, such as illustrated in FIGS. 10A and 10B.

Corresponding reference numerals indicate corresponding parts throughout the several views of the drawings.

DETAILED DESCRIPTION

Example embodiments will now be described more fully with reference to the accompanying drawings.

Micromachining processes have enabled high performance and low cost microsensors that are customizable for a wide range of applications. Significant interest has been directed at the development of systems with miniature sensors for harsh environmental conditions, such as found in the oil and natural gas industry. The present disclosure relates to an in situ high-resolution distributed pressure measurement system for core-flood experiments, where a series of microfabricated pressure sensors are embedded along the length of a rock core, for example embedded in bolts positioned along the rock core. The microfabricated pressure sensors can be embedded within bolts positioned along the seam of the rock core within a sheath that encases the rock core. In such instances, in order to ensure the rock core remains flush with the sheath, the interface electronics can be located outside the sheath. The pressure sensors can communicate with interface electronics using a hermetic lead transfer, and in certain instances, wireless means.

An example high-resolution distributed pressure measurement system 10 for use in core-flood experiments is illustrated in FIG. 1. The system 10 comprises an enclosure 12 and a sheath 14 disposed within the enclosure 12. The enclosure 12 defines a high-pressure ("HP") chamber 15 having a pressure less than or equal to about 250 bar and a temperature of about 125° C. For example, the high-pressure chamber 15 may comprise an oil bath having a pressure less than or equal to about 250 bar and a temperature of about 125° C. To maintain the high pressure in the high-pressure chamber 15, a pump 13 may be in fluid communication with the chamber 15. The oil bath may include one or more chemically compatible liquids, such as inert nonconductive fluids and oils like mineral oil. In certain instances, the high-pressure chamber 15 may also include one or more conductive fluids. In such instances, the printed circuit board ("PCB") 21 may need to be insulated so as to avoid any exposed electrical contact with the conductive fluid. As illustrated, the enclosure 12 may have a cylindrical shape. However, the skilled artisan will appreciate that various other shapes are conceivable. The enclosure 12 can be made of one or more materials, including, for example, stainless steel or alloys or other high tensile strength materials that can be used to make high-pressure vessels and that are also relatively inert.

The sheath 14 defines an interior tube 17 that extends along a longitudinal axis 20. The interior tube 17 is configured to receive a core sample (not shown) therein. The tube 17 may define a low-pressure ("LP") chamber having an interior fluidic pressure greater than or equal to about 1 bar to less than or equal to about 20 bar (i.e., 2 MPa, 290 psi). The high-pressure chamber 15 may be at a pressure greater than the fluid in the low-pressure chamber 17. A plurality of pressure sensors 16 can be embedded in the sheath 14, and at least one controller (e.g., receiver circuit) 18 can be positioned outside of the sheath 14 and the enclosure 12, as illustrated. The sheath 14 can be made of a polymer or another comparable material (such as, VITON® polymers). As illustrated, the sheath 14 may have a cylindrical shape. However, the skilled artisan will appreciate that various other shapes are conceivable.

During core-flood experiments, the sheath 14 and the rock core positioned in the interior chamber 17 of the sheath 14 work to isolate any fluid within the interior chamber 17 from the high pressure in chamber 15. During permeability experiments, a gaseous or liquid phase fluid can be transported through the rock core in the low-pressure chamber 17 in the longitudinal direction 20. Such permeability experiments can be months in duration. During such time, pressure can be measured along the surface of the core sample using the plurality of sensors 16 embedded in the sheath 14.

Each pressure sensor 16 is configured to measure pressure along the surface of the core sample. For example, the pressure sensors 16 can measure pressure by detecting changes in electrical capacitance. In certain instances, the pressure sensors 16 are grouped into pressure sensor subsets. In each subset, the pressure sensors 16 can be arranged symmetrically around the longitudinal axis 20 of the sheath 14. For example, in certain instances, the pressure sensors 16 may be spaced 120 degrees apart, as illustrated in FIG. 2A. In other instances, such as illustrated in FIG. 2B, the pressure sensors 16 may be spaced 90 degrees apart. Though not illustrated, the skilled artisan will appreciate that various other arrangements are also contemplated by this disclosure.

With renewed reference to FIG. 1, in certain instances, the plurality of pressure sensors 16 can be in wired communication with a controller (e.g., external receiver circuit) 18 that is disposed outside of the enclosure 12. For example, the pressure sensors 16 can be electrically coupled to the controller 18 via a printed circuit board ("PCB") 21. Though not limited to, in certain instances, the printed circuit board 21 may be a flexible printed circuit board. For example, the PCB 21 can include four pressure sensors 16 located on tabs 22 and interface electronics (not shown) located along a backbone 23. As illustrated, the sensors on the PCB tabs can be positioned along the length of the rock core, for example, within feedthroughs in the sheath 14 (as discussed below in the context of FIGS. 4 and 5A-5C), where the electronics (not shown) on the backbone 23 of the PCB 21 are located in the high-pressure chamber 15. A feedthrough that traverses the enclosure 12 can connect the PCB 21 to the controller 18. The controller 18 can read and record sensor data using, for example only, an I²C bus. The controller 18 provides power to the PCB 21. In one example, the controller 18 is based on the Raspberry Pi® computer from the Raspberry Pi Foundation, UK. Upon request, the recorded data can be transferred from the controller 18 to a remote computer 19 for data processing. For example, the recorded data can be wirelessly transferred through a Wi-Fi network.

Figure 3:
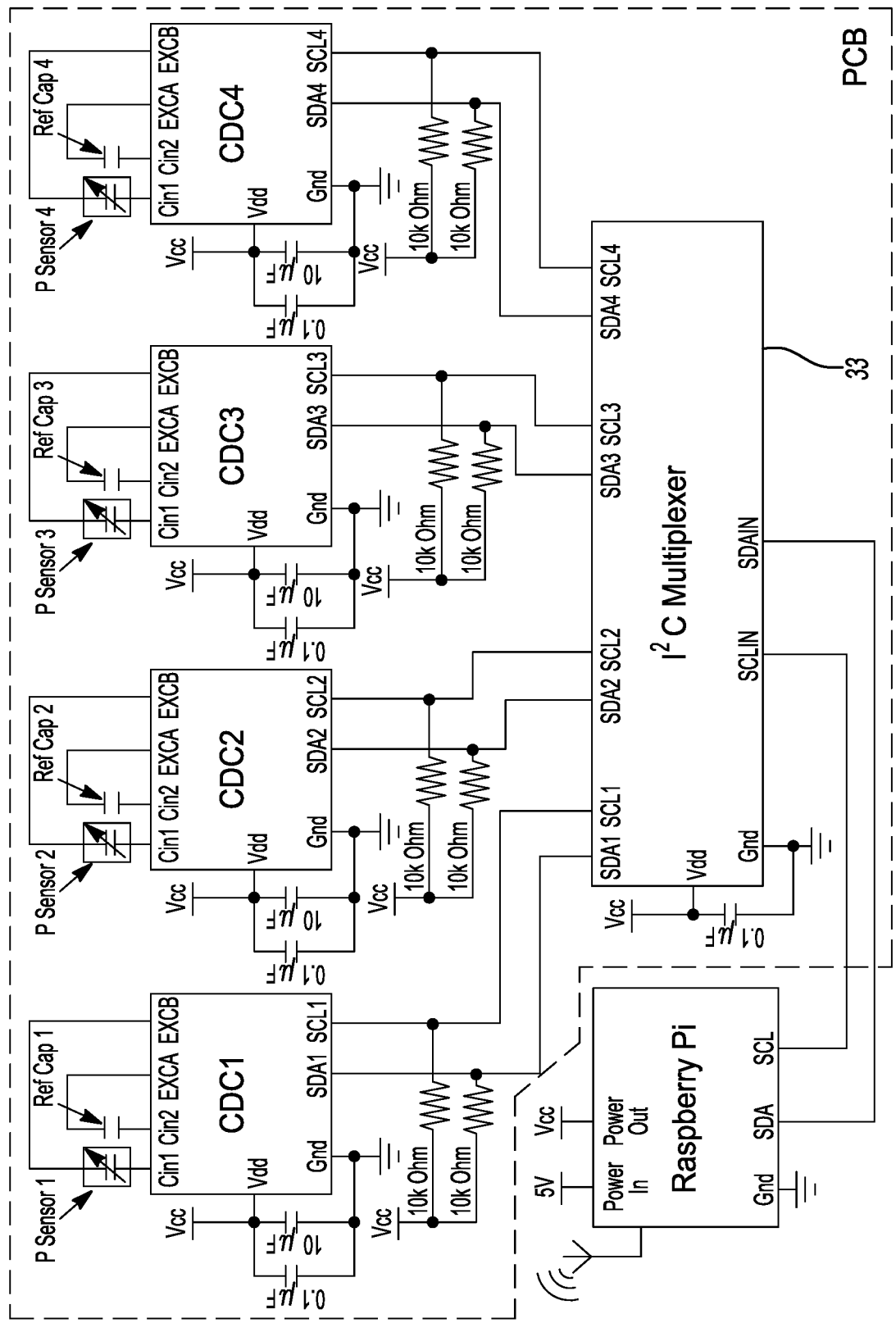
FIG. 3 is a schematic of a circuit used in an example embodiment of the pressure measurement system.
Figure 4A:
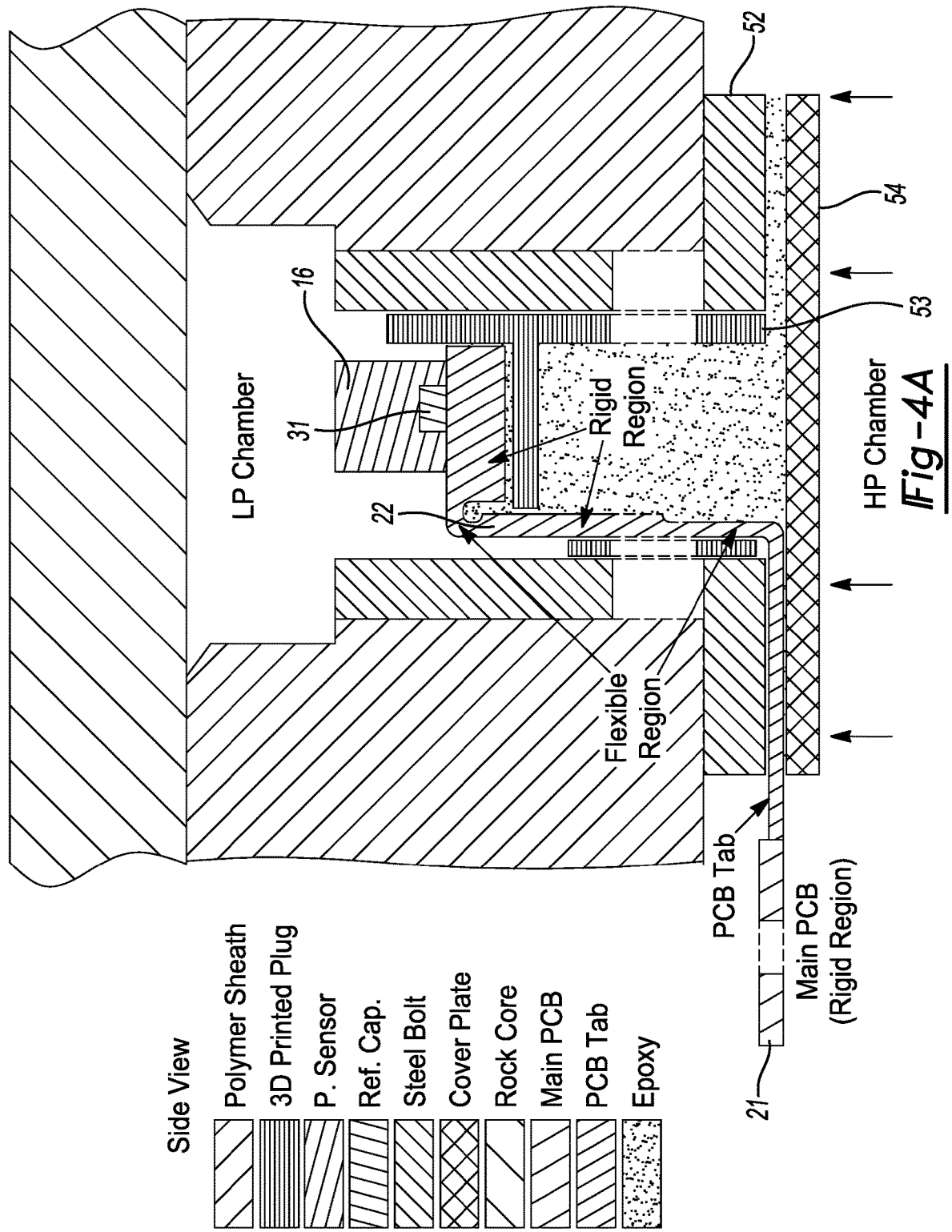
FIG. 4A is a cross-sectional view of an example feedthrough for use within the high-resolution distributed pressure measurement system illustrated in FIG. 1.
Figure 4C:
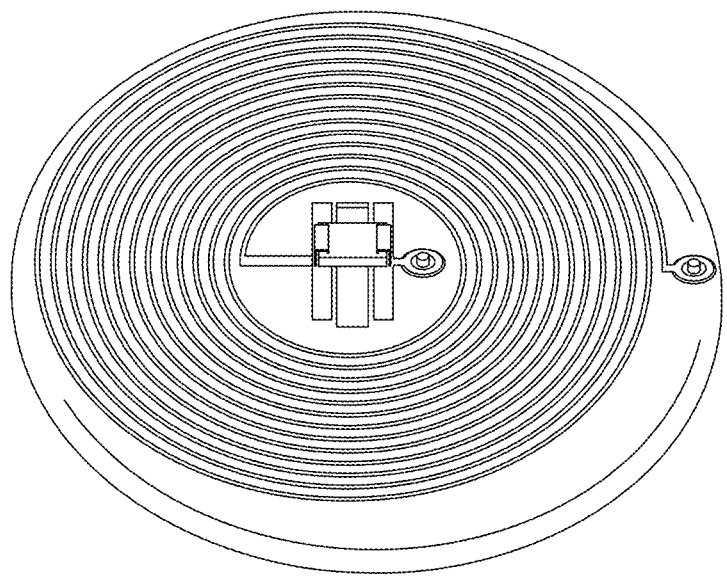
FIG. 4C is an illustration of an example LC sensor module having a coil that permits inductive coupling and a capacitive pressure sensor mounted in the center of the coil.
Figure 4D:
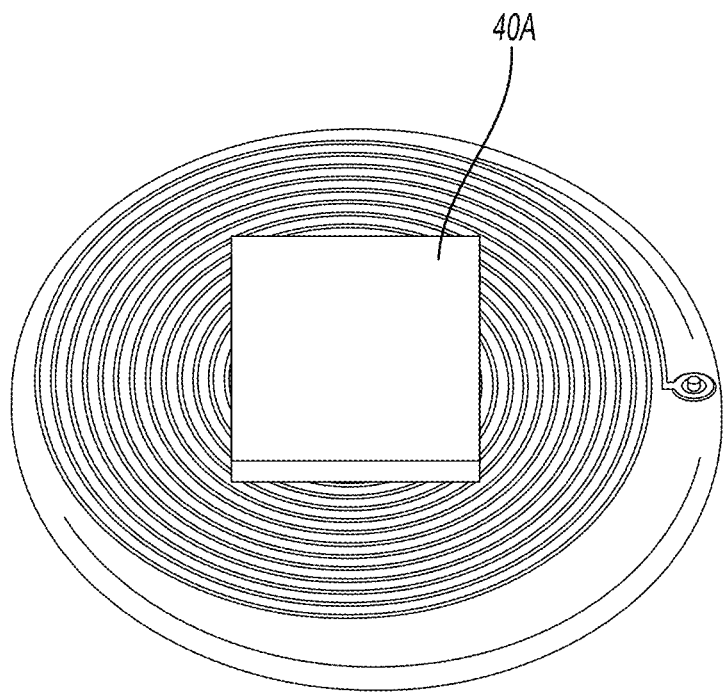
FIG. 4D is an illustration of the example LC sensor module illustrated in FIG. 4C having a metal cover on top.
Figure 4E:
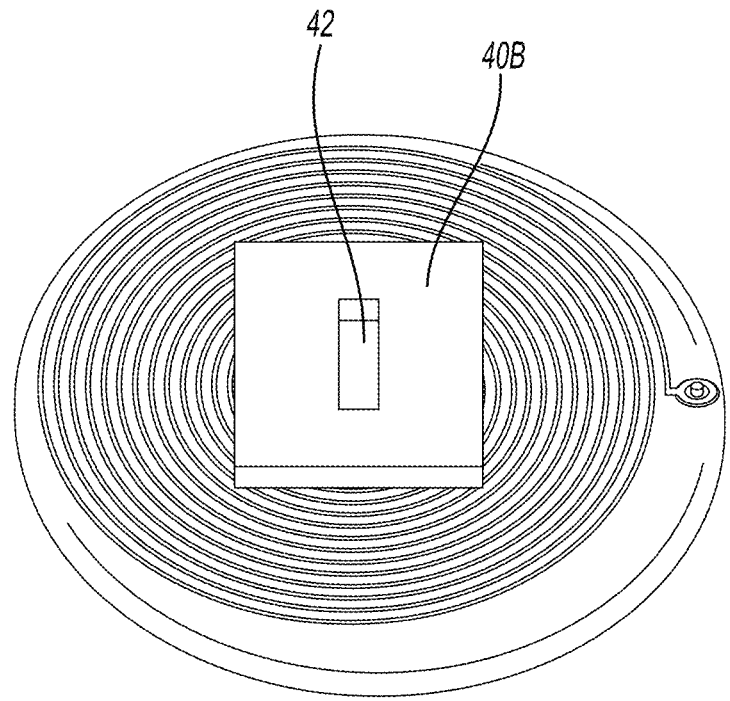
FIG. 4E is an illustration of the example LC sensor module illustrated in FIG. 4C having a metal cover on bottom.

Referring to FIG. 3, the flexible circuit board 21, which uses polyimide as the base material (Flex PCB, Santa Ana, USA), consists of the backbone with the sensor interface electronics, and four narrow tabs with a pressure sensor 16 and a reference capacitor ("Ref. Cap.") 31 at the distal tips. The reference capacitor 31 has negligible temperature dependence and is used to compensate for the temperature dependence of the capacitance readout circuit and other common-mode artifacts. Four commercial capacitive pressure sensors (e.g., SCB10H, Murata Manufacturing Co., Ltd., Japan) are used in the system. These sensors have a dynamic range of 25 bar and sensitivity in the range of 1.3-6.5 fF/kPa. Four capacitance-to-digital converter (CDC) chips 32 (AD7746, Analog Devices Inc., USA) and an I²C multiplexer 33 (LTC4306, Linear Technology Corp., USA) are used for selective capacitance readout from the four sensor channels. The estimated pressure resolution of the sensor and CDC chip combination is 0.25-0.83 mbar (theoretical). As illustrated in FIG. 4A, the tabs can be bent and inserted into the feedthrough on the polymer sheath such that the sensor at the tip of the tab can measure the pressure in the LP chamber. Other types of capacitive pressure sensors may also be used. Piezoresistive pressure sensors may also be used; however, the use of piezoresistive pressure sensors would require the use of appropriate analog-to-digital converters.

Figure 5A:
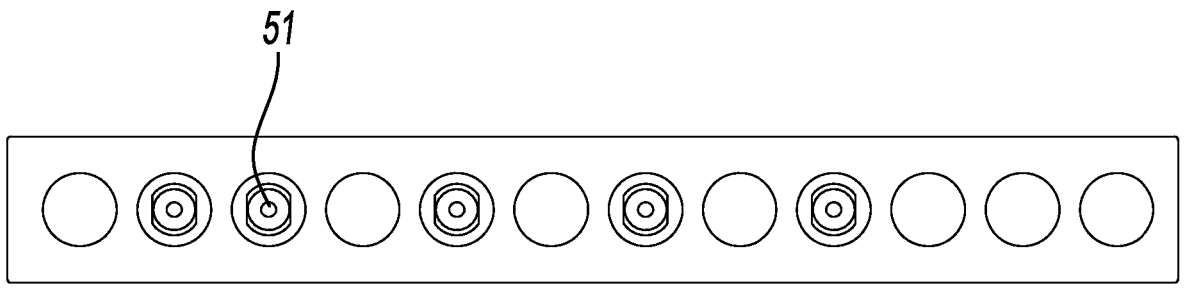
FIG. 5A illustrates a sheath with steel nuts for use within a high-resolution distributed pressure measurement system in accordance with various aspects of the current technology.
Figure 5B:
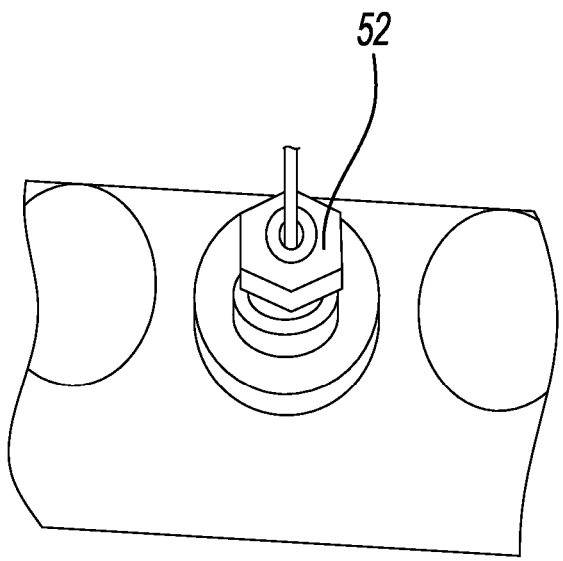
FIG. 5B illustrates a threaded plug mated with the steel nut illustrated in FIG. 5A.
Figure 5C:
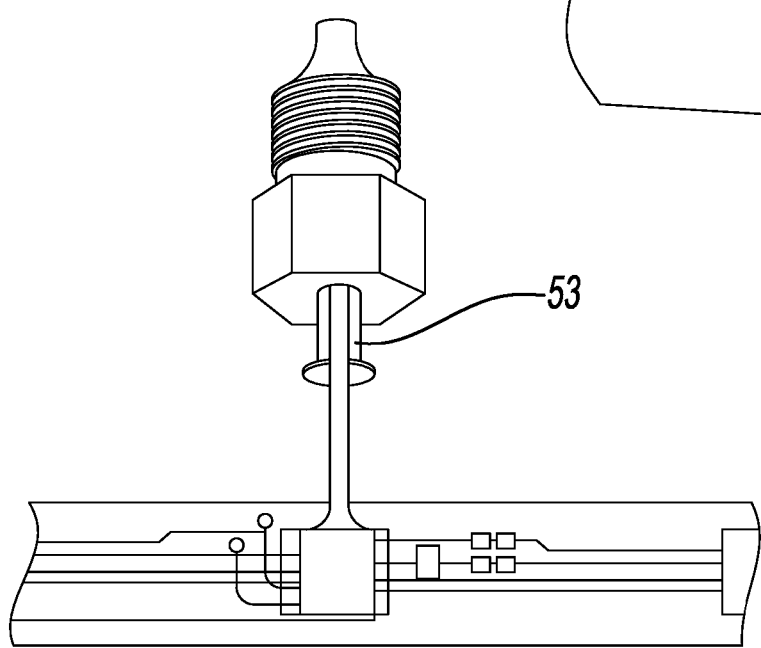
FIG. 5C illustrates a tab extending from a printed circuit board and into a hole of the threaded plug illustrated in FIG. 5B.

As illustrated in FIG. 4A, a customized feedthrough can be used to provide lead transfer between the sensors 16 and the interface electronics (not shown) through the sheath 14, across a 230-bar pressure difference. The sheath 14 used in a typical core-flood test cell is shown in FIG. 5A. In this embodiment, the sheath 14 includes steel nuts 51 that are sealed with steel bolts 52 that incorporate a mating thread. As illustrated in FIG. 5B, the steel bolt 52 is perforated to accommodate a 3D-printed plug 53. As illustrated in FIG. 5C, the 3-D printed plug 53 is used as an insert for mounting the PCB tab 22 within the perforation. The 3D-printed plug can be made from M3 crystal resin using the ProJet® 3500 HDMax 3D printer (3D Systems, Rock Hill, USA). The tab 22 can is inserted into the perforation on the steel bolt. As illustrated in FIG. 4A, the distal end of the PCB tab 22 with the pressure sensor 16 and the reference capacitor 31 can be bent at 90° such that the sensing diaphragm faces the low-pressure chamber 17, In certain instances, epoxy can be used to fill the interior of the 3D-printed insert and/or a cover plate 54 can be placed over the perforation to isolate the pressure from the high-pressure chamber 15.

Figure 6A:
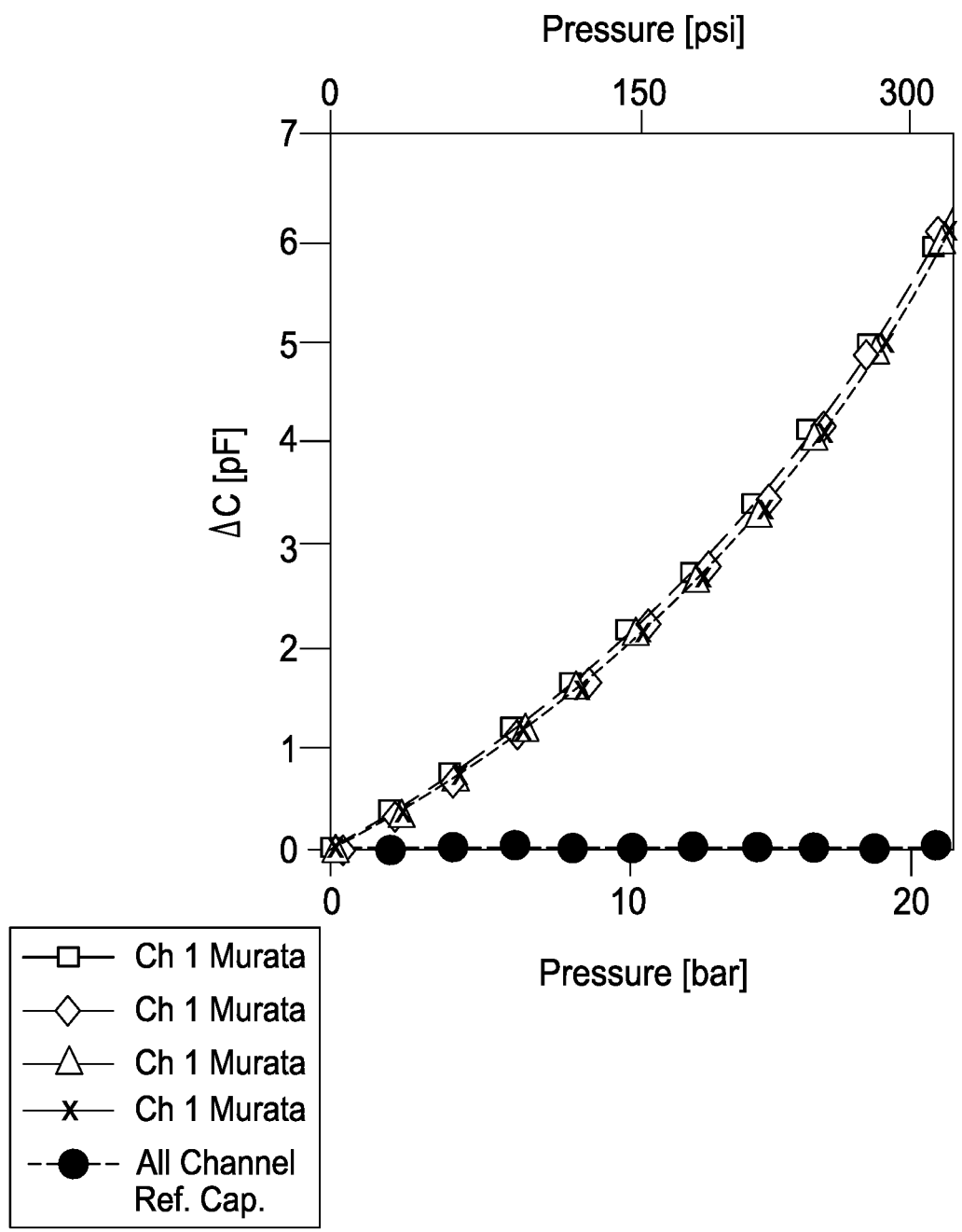
FIG. 6A is a graph showing the capacitive response of the pressure sensors with chamber pressure at room temperature.
Figure 6B:
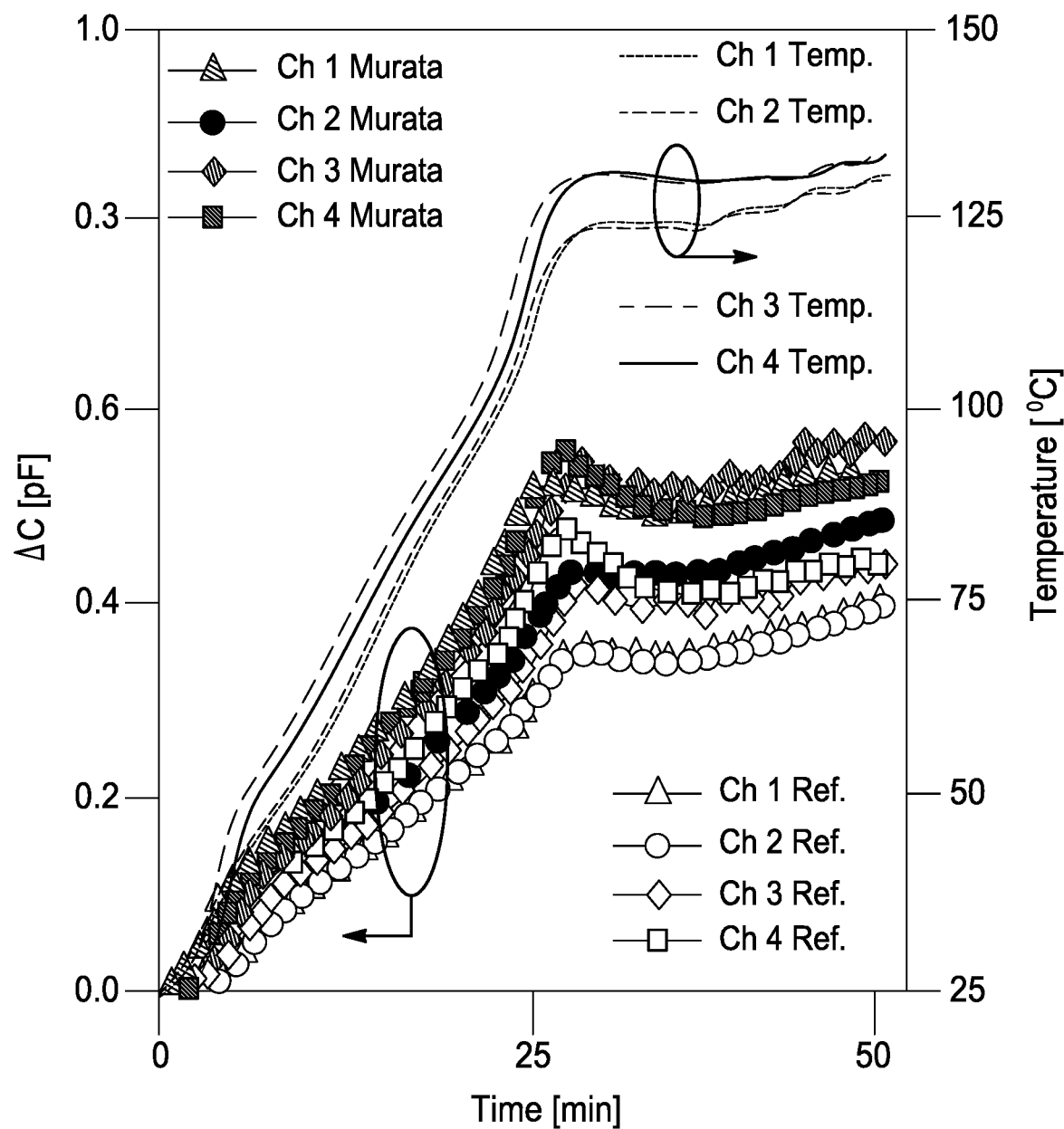
FIG. 6B is a graph showing the capacitive output of the pressure sensors with varying ambient temperature at atmospheric pressure.

Experimental characterization of the PCB, combined with finite element analysis performed using COMSOL Multiphysics® indicated that the system is significantly affected by residual stress in the solder joints that bond the sensor contacts to the metal pads on the printed circuit board. To address this issue, an anneal protocol was developed. The printed circuit board was located in an oven where the temperature was raised from room temperature to 170° C. at 3° C./min and then held steady for 5 hour at 170° C. After this step, the PCB was allowed to cool. FIG. 6B shows the post-anneal system temperature response at atmospheric pressure indicating successful system operation up to about 125° C.

The pressure response of the system 10 was first recorded at room temperature in a test chamber pressurized with nitrogen gas. The recorded capacitance change ($\Delta C$) with chamber pressure of a typical system is shown in FIG. 6A. All four pressure sensors demonstrated consistent and overlapping $\Delta C$ responses. The measured sensitivity of the system was 1.5-5.5 fF/kPa.

FIGS. 10A and 10B illustrate other example high-resolution distributed pressure measurement systems 100A, 100B for use in core-flood experiments. Like the system 10 illustrated in FIG. 1, systems 100A and 100B each include an enclosure 112 and a sheath 114 disposed within the enclosure 112. The enclosures 112 define a high-pressure chamber 115. The sheaths 114 define a low-pressure chamber 117. A plurality of sensor modules LC1-LC4 comprising pressure sensors (such as illustrated in FIGS. 4A-4F) can be distributed inside each sheath 114 so that the pressure sensors can measure the pressure on the surface of a rock core (not shown) disposed within the low-pressure chamber. Sensor data can be collected by the readout node 102 and stored in the MCU0BLE module 104. Either a wireless or wired connection may be made between the Readout PCT 121 to the external unit controller 118. For example, FIG. 10A illustrates a wireless connection, and FIG. 10B illustrates a wired connection, as well as FIG. 4B. Each connection is configured to transfer the recorded data to the Readout PCB 121. Upon request, the recorded data can be transferred from the controller 118 to a remote computer 119 for data processing. For example, the recorded data can be wirelessly transferred through a Wi-Fi network.

Figure 4F:
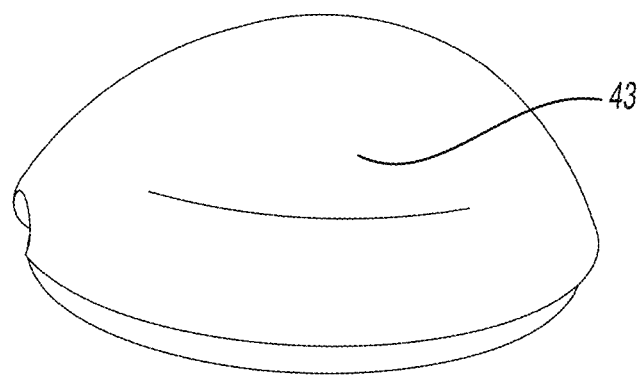
FIG. 4F is an illustration of the example LC sensor module illustrated in FIG. 4C encased in a flexible epoxy.

FIG. 11B illustrates an example pressure sensor module, such as would be include, for example, in systems 100A and/or 100B, as illustrated in FIGS. 10A and 10B, respectively. As illustrated in FIG. 11B, a LC sensor module 300 may be comprised of an inductive coil 302, capacitive pressure sensor 304, and packaging material, which includes for example an epoxy encapsulation 43. The inductive coil 302 may be formed on a flexible PCB. The capacitive pressure sensor 304 can be electrically attached to the inductive coil 302. In certain instances, stiff metal covers 40A, 40 may be placed on the top and bottom of the LC sensor module's flexible PCB capping the capacitive pressure sensor so as to provide protection, such as more specifically illustrated in FIGS. 4D and 4E. These covers 40A, 40B may protect the capacitive pressure sensor from shearing forces during insertion, and from and delamination and detachment from the inductive coil flexible PCB. The top and bottom of the metal covers 40A, 40B may be curved so as to match curvature of the rock core and polymer sheath. In certain instances, the bottom metal cover 40B can include a slot 42 so as to allow transmission of pressure to the capacitive pressure sensor. In certain instances, as illustrated in FIG. 4F, the LC sensor module can be fully encapsulated in a flexible mold 43 (such as VITON® epoxy) so as to provide further mechanical and chemical protection. VITON® epoxy is resistant to corrosive chemicals and is sufficiently flexible to permit the transmission of pressure to the sensor.

The sensor modules LC1-LC4 can be formed on a printed circuit board, which can be disposed adjacent, for example attached to, the interior surface or wall 120 of the sheath 114. Each sensor module LC1-LC4 can have a corresponding readout node 102. As illustrated, the node 102 may be aligned adjacent to and in close proximity to the corresponding LC sensor module. This will permit wireless communication through the polymer sheath 114, in contrast to system 10 illustrated in FIGS. 1 and 4A. An example sensor module, such as sensor modules LC1-LC4, illustrated in FIG. 10A, is illustrated in FIG. 11A. As illustrated, the sensor module includes one or more pressure sensors 116 and a sense coil 124 disposed on a circuit board 113. In this example, the sensor module includes one or more capacitive pressure sensors 116 assembled on a miniature PCB 113 (e.g., three sensors illustrated, each with a size of 1.7×0.9 mm2). The pressure sensors 116 and the sense coil 124 form an LC sensor module such that a change in capacitance of the pressure sensor 116 will result in a change in the resonant frequency of the sensor module. Changes in the resonant frequency will in turn be wirelessly detected by a readout coil 122 and associated circuit in the readout node 102, as illustrated in FIG. 12, which provides an example implementation for the circuitry of the readout node 102. The frequency shift will be converted to voltage output by the readout node circuit. This voltage will be detected by the analog-to-digital converter in a module that may combine MCU functionality with Bluetooth Low Energy (BLE) communication, such as Silicon Labs BGM121 Blue Gecko module.

With renewed reference to FIG. 10A, the MCU-BLE module 104 can establish either a wireless BLE link to an external unit 118 or a wired link to an external unit 118 through an electrical feedthrough in the cell exterior end cap. The external unit 118 can be used for system control and data management. In one example, the external unit 118 will be based on Raspberry Pi and will be able to upload the data to cloud storage, and also wirelessly interact with a remote Windows computer 119 through a Wi-Fi link. The PCB 121 can be powered by a high temperature coin cell lithium battery, such as Panasonic BR2477A battery that has an operating temperature of between about −40 and about 125° C., capacity of 1000 mAh, a diameter of 24.5 mm, and a thickness of 7.7 mm. Alternatively, if a single two-wire cable is allowed to run through the cell exterior end cap, an external power supply can be used to power the PCB so that long term operation can be performed.

In yet various other aspects, the present disclosure provides a method for preparing and using a system, such as example high-resolution distributed pressure measurement systems 100A and 100B, illustrated in FIGS. 10A and 10B, respectively. In preparation for testing, a rock core is normally inserted into heat shrinking tubing. The encased rock core may then be inserted into a polymer sheath. This rock core-polymer sheath assembly this may be then placed into the low-pressure chamber 117. In accordance with various aspects of the current disclosure, to incorporate the LC sensor module onto the rock core, a hole can be milled into the heat shrink tubing and the LC sensor module can be placed into this hole. The LC sensor module may be held in place using, for example only, epoxy. The encased rock core may then be inserted into polymer sheath 114. The readout PCB 121 may be then positioned against the polymer sheath 114 so as to permit inductive coupling between the LC sensor module and Readout PCB 121 for sensor readout. This assembly may be then placed into the test chamber 115 (composed of the Cell Exterior Wall 112 and Cell Exterior End Caps). A connection can be established between external unit 118 and the sensor readout either by a wireless link or an electrical feedthrough in the Cell Exterior End Cap between the Readout PCB 121.

Certain features of the current technology are further illustrated in the following non-limiting examples.

Examples

An example high-resolution distributed pressure measurement system, like system 10 illustrated in FIG. 1, was prepared in accordance with various aspect of the present disclosure. The example system can be subjected to distributed pressure measurement and flow tests. For example, FIG. 7 illustrates example conditions for a distributed pressure test for example high-resolution distributed pressure measurement system, for example, like the system illustrated in FIG. 1.

Figure 7:
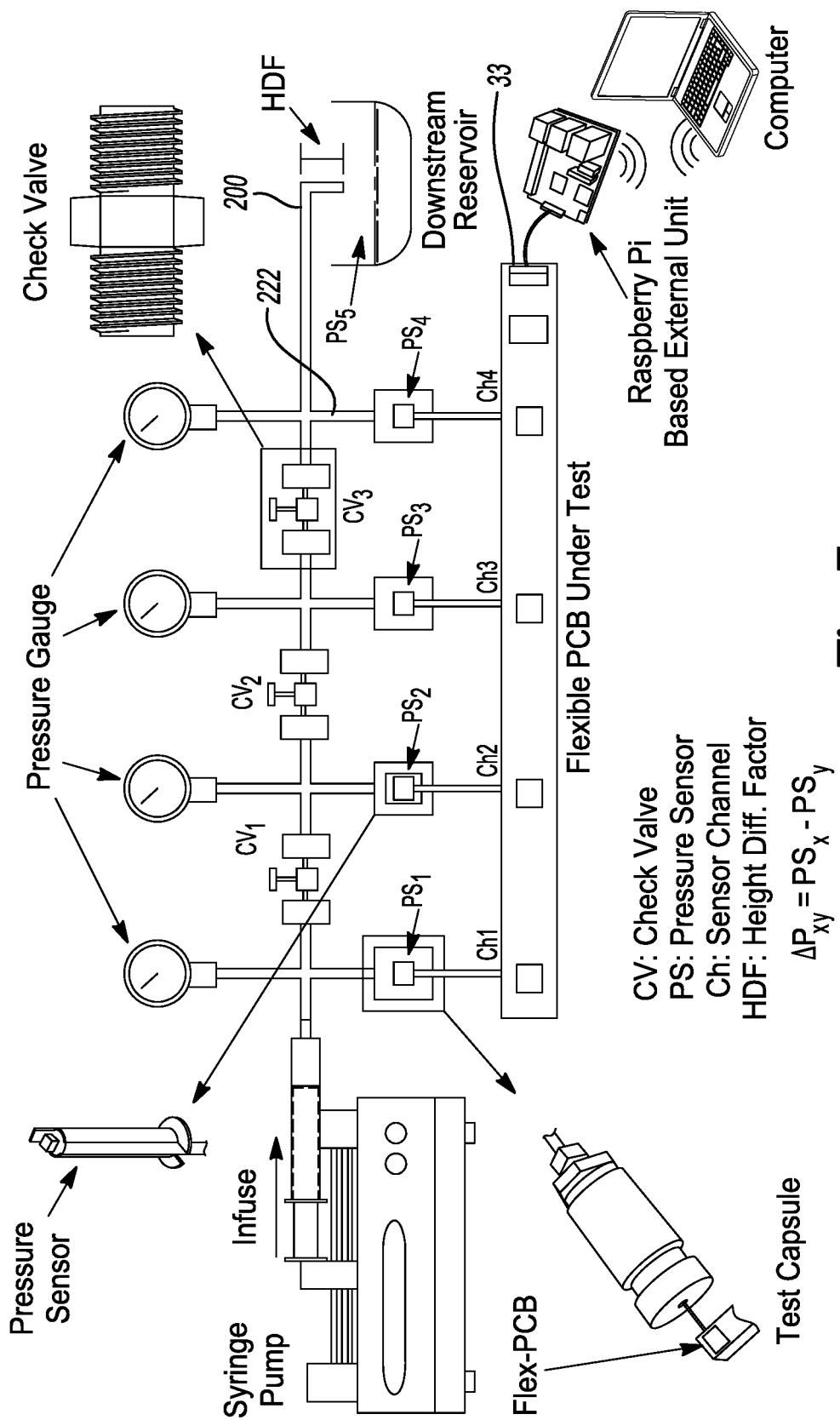
FIG. 7 is an illustration of example conditions for a distributed pressure test for example high-resolution distributed pressure measurement system, for example, like the high-resolution distributed pressure measurement system illustrated in FIG. 1.

As illustrated in FIG. 7, the test may include a syringe pump-driven fluid channel 200 with spring-operated check valves ($CV_x$) located between four test capsules where the PCB tabs 222 were inserted. $CV_1$ and $CV_2$ had 6.2 mbar (0.09 psi) opening pressure while $CV_3$ had 146.1 mbar (2.12 psi) opening pressure at 25 ml/min flow rate. The replaceable check valves created a pressure differential between adjacent pressure sensors ($PS_1$, $PS_2$, $PS_3$, $PS_4$). This differential pressure can be used to characterize the resolution and gradient measurement capability of the example system. Pressure gauges can be included in the test setup to provide reference readings. White mineral oil can be used as test fluid.

Figure 8:
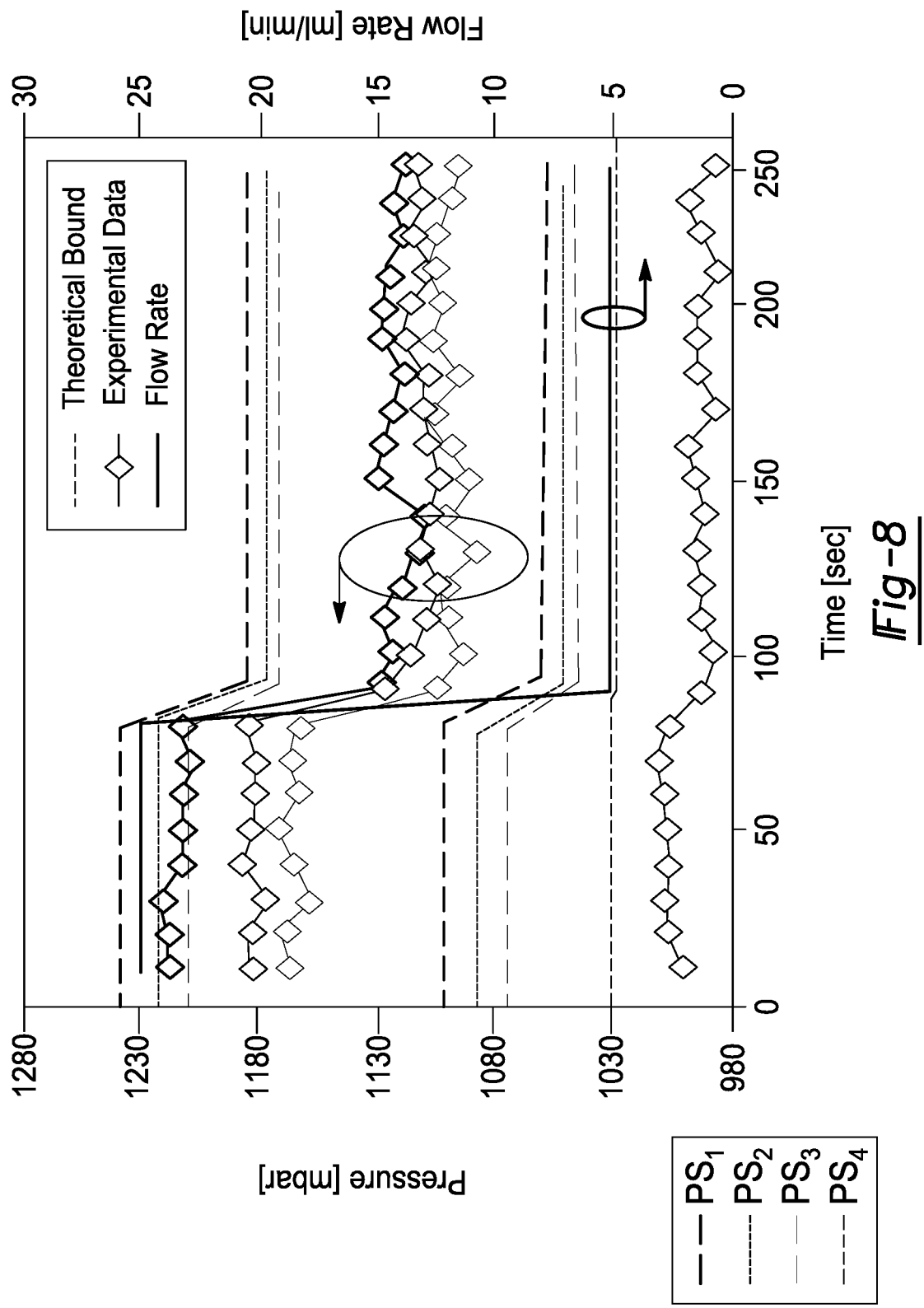
FIG. 8 is a graph showing pressure response of the pressure sensors during flow test at room temperature.
Figure 9:
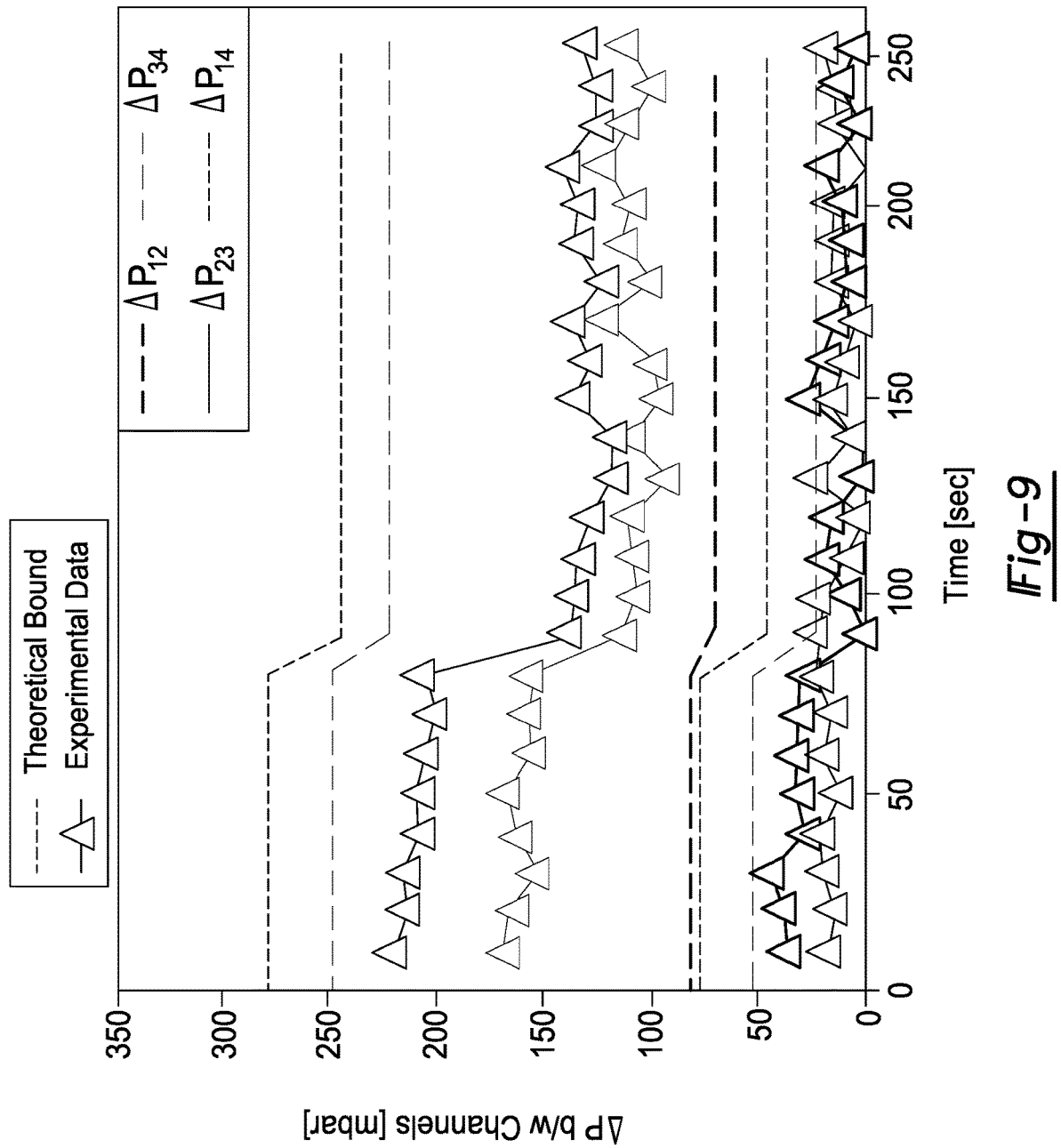
FIG. 9 is a graph showing differential pressure between different test capsules (tabs) recorded during the flow test at room temperature.

In a typical experiment, a fluid infusion rate of 25 ml/min can be maintained for the first 90 seconds followed by a reduced infusion rate of about 5 ml/min through the rest of the experiment. FIG. 8 shows a time-series of pressure measurements, sampled at 10 second intervals from the four sensors. The flow rate during the experiment is also plotted. FIG. 9 shows the differential pressure between different test capsules (i.e., tabs). The theoretically estimated bounds for the response based on the test setup configuration and experimental conditions are also plotted. As expected, the pressure drops between channels 1, 2, and 3 were small, whereas the pressure drop between channels 3 and 4 was large. These are consistent with the opening pressure of the check valves placed between each channel pair. The measured pressure gradients are well within the theoretically estimated bounds. These results demonstrated the capability of this system to measure pressure gradient with a resolution as small as 0.3 mbar. Small deviations may be caused by a variety of factors, including local variations in the flow rate.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A distributed pressure measurement system comprising:
   an enclosure that defines a high-pressure chamber;
   a sheath disposed within the high-pressure chamber, the sheath defining a tube that extends along a longitudinal axis and that is configured to receive a core sample;
   a plurality of pressure sensors embedded in the sheath and disposed along the longitudinal axis of the tube, wherein each pressure sensor is configured to measure pressure at a predetermined position along the surface of the core sample; and
   one or more sensor modules distributed on an interior-facing surface of the sheath, wherein each sensor module includes at least one pressure sensor of the plurality of pressure sensors disposed on a circuit board and a sense coil formed on the circuit board.

2. The distributed pressure measurement system of claim 1, wherein the plurality of pressure sensors measure pressure by detecting changes in electrical capacitance.

3. The distributed pressure measurement system of claim 1, wherein the plurality of pressure sensors are grouped into subsets of pressure sensors such that the pressure sensors in a given subset of pressure sensors are arranged around the longitudinal axis of the tube and symmetrically to each other.

4. The distributed pressure measurement system of claim 3, wherein each pressure sensor in a given subset of pressure sensors is spaced 120 degrees apart from other pressure sensors in the respective subset.

5. The distributed pressure measurement system of claim 3, wherein each pressure sensor in a given subset of pressure sensors is spaced 90 degrees apart from other pressure sensors in the respective subset.

6. The distributed pressure measurement system of claim 1, further comprises at least one receiver circuit positioned outside of the enclosure, wherein the plurality of pressure sensors communicate pressure measurements to the at least one receiver circuit.

7. The distributed pressure measurement system of claim 1, wherein the one or more pressure sensors and the sense coil form an LC sensor module such that changes in capacitance by the plurality of the pressure sensors causes a change in resonant frequency of the LC sensor module.

8. The distributed pressure measurement system of claim 7, further comprising one or more readout nodes arranged outside of the sheath, such that each readout node is aligned adjacent to a corresponding sensor module, wherein each readout node includes a readout coil inductively coupled to the sense coil of the corresponding sensor module and a readout circuit configured to detect changes in resonant frequency of the LC sensor module.

9. The distributed pressure measurement system of claim 8, wherein the one or more readout nodes are disposed on an exterior surface of the sheath and are configured to communicate with a controller disposed outside of the enclosure.

10. The distributed pressure measurement system of claim 1, wherein the plurality of pressure sensors are encapsulated in a flexible mold.

11. A distributed pressure measurement system comprising:
   an enclosure that defines a high-pressure chamber;
   a sheath disposed within the high-pressure chamber, the sheath defining a tube that extends along a longitudinal axis and that is configured to receive a core sample;
   a plurality of pressure sensors embedded in the sheath and disposed along the longitudinal axis of the tube, wherein each pressure sensor is configured to measure pressure at a predetermined position along the surface of the core sample;
   a controller in wired communication with the plurality of pressure sensors, wherein the controller is disposed outside of the enclosure;
   a plurality of plugs, wherein each plug is received by a feedthrough hole formed in the sheath and is configured to host one of the plurality of pressure sensors; and
   a circuit board disposed on an exterior surface of the sheath and electrically coupled to each of the plurality of pressure sensors.

12. The distributed pressure measurement system of claim 11, wherein the plurality of pressure sensors are grouped into subsets of pressure sensors such that the pressure sensors in a given subset of pressure sensors are arranged around the longitudinal axis of the tube and symmetrically to each other.

13. The distributed pressure measurement system of claim 12, wherein each pressure sensor in a given subset of pressure sensors is spaced 120 degrees apart from other pressure sensors in the respective subset.

14. The distributed pressure measurement system of claim 12 wherein each pressure sensor in a given subset of pressure sensors is spaced 90 degrees apart from other pressure sensors in the respective subset.

15. The distributed pressure measurement system of claim 11, wherein the plurality of pressure sensors are encapsulated in a flexible mold.

16. A distributed pressure measurement system comprising:
   an enclosure that defines a high-pressure chamber;
   a polymeric sheath disposed within the high-pressure chamber and defining a low-pressure chamber that extends along a longitudinal axis and that is configured to receive a core sample;
   a plurality of pressure sensors embedded in the sheath and disposed along the longitudinal axis of the low-pressure chamber, wherein the plurality of pressure sensors are grouped into one or more subsets of pressure sensors, wherein each subset includes at least one pressure sensor of the plurality of pressure sensors and in each given subset of pressure sensors having two or more pressure sensors the pressure sensors are arranged around the longitudinal axis of the low-pressure chamber and symmetrically to each other; and
   one or more sensor modules distributed on an interior-facing surface of the sheath, wherein each sensor module includes the plurality of pressure sensors disposed on a circuit board and a sense coil formed on the circuit board, wherein the plurality of pressure sensors and the sense coil form an LC sensor module such that changes in capacitance by the one or more pressure sensors causes a change in resonant frequency of the LC sensor module.

17. The distributed pressure measurement system of claim 16, wherein the plurality of pressure sensors measure pressure by detecting changes in electrical capacitance.

18. The distributed pressure measurement system of claim 16, further comprising at least one receiver circuit positioned outside of the enclosure, wherein the plurality of pressure sensors communicate pressure measurements to the at least one receiver circuit.

19. The distributed pressure measurement system of claim 16, further comprising one or more readout nodes arranged outside of the sheath, such that each readout node is aligned adjacent to a corresponding sensor module, wherein each readout node includes a readout coil inductively coupled to the sense coil of the corresponding sensor module and a readout circuit configured to detect changes in resonant frequency of the LC sensor module.

20. The distributed pressure measurement system of claim 19, wherein the one or more readout nodes are disposed on an exterior surface of the sheath and are configured to communicate with a controller disposed outside of the enclosure.

* * * * *